United States Patent
Liu et al.

(10) Patent No.: US 10,612,007 B2
(45) Date of Patent: Apr. 7, 2020

(54) **METHOD FOR INCREASING CITRIC ACID PRODUCTION BY *ASPERGILLUS NIGER* FERMENTATION**

(71) Applicants: Jiangnan University, Wuxi (CN); JIANGSU GUOXIN UNION ENERGY CO LTD, Wuxi (CN)

(72) Inventors: Long Liu, Wuxi (CN); Jian Chen, Wuxi (CN); Guocheng Du, Wuxi (CN); Jianghua Li, Wuxi (CN); Xian Yin, Wuxi (CN); Zhijie Hu, Wuxi (CN); Jianwei Jiang, Wuxi (CN); Fuxin Sun, Wuxi (CN); Sai Jin, Wuxi (CN); Cheng Zhang, Wuxi (CN); Xiaodong Jiang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 42 days.

(21) Appl. No.: 15/867,836

(22) Filed: Jan. 11, 2018

(65) Prior Publication Data
US 2018/0195052 A1 Jul. 12, 2018

(30) Foreign Application Priority Data
Jan. 12, 2017 (CN) .......................... 2017 1 0022534

(51) Int. Cl.
*C12N 15/80* (2006.01)
*C12P 7/48* (2006.01)
*C12N 9/02* (2006.01)

(52) U.S. Cl.
CPC ............ *C12N 9/0008* (2013.01); *C12N 15/80* (2013.01); *C12P 7/48* (2013.01); *C12Y 102/01076* (2013.01)

(58) Field of Classification Search
None
See application file for complete search history.

(56) References Cited

PUBLICATIONS

Show et al. Overview of citric acid production from *Aspergillus niger*. Published online Apr. 20, 2015. Frontiers in Life Science. vol. 8, No. 3, p. 271-283. (Year: 2015).*

* cited by examiner

*Primary Examiner* — Channing S Mahatan
(74) *Attorney, Agent, or Firm* — IPro, PLLC

(57) ABSTRACT

The invention discloses a method for improving citric acid production by *Aspergillus niger* fermentation, which integrates *Aspergillus niger* GABA pathway succinate semialdehyde dehydrogenase SSD gene into *Aspergillus niger* genome to obtain recombinant *Aspergillus niger* strain, and uses recombinant black The *Aspergillus* strain ferments to produce citric acid; the expression of the succinate semialdehyde dehydrogenase SSD gene is regulated by the Pgas promoter. The method of the invention realizes the expression of succinate semialdehyde dehydrogenase SSD in *Aspergillus niger* to enhance the GABA pathway so as to strengthen the TCA cycle and promote the synthesis of citric acid.

20 Claims, No Drawings
Specification includes a Sequence Listing.

SEQUENCE LISTING

<160> NUMBER OF SEQ ID NOS: 14

<210> SEQ ID NO 1
<211> LENGTH: 1491
<212> TYPE: DNA
<213> ORGANISM: Aspergillus niger

<400> SEQUENCE: 1

```
atgggttaca ctgtccctcc gctcaaagac caatccctct tcattcaaaa ggcatacgtc      60
aatggcgagt gggtagatgc tcagtccgga cagaccttcg aagtccacga ccctgcctcc     120
ggaaaactca tcggaacaag tcccgaattc tccgccgcag acaccgagaa ggccatccaa     180
gccgccaaag aagccttccc caaattccgc acaaccctgt cccgcgagcg cgcccgcatg     240
ctgcgcagat ggtaccagct catgatcgac aatgccgacg acctagccac cctgataacc     300
tgggaaaacg gaaagccgct caccgacgcc aaaggcgagg tgaactacgc ggccagcttc     360
ttcgaatggt tcagcgaaga agctcccgc atctacggtg acaccatccc atcctccgtc      420
cccggcaacc gggtcatgac cctgaagcaa cccgtcggcg tctgtggtct catcacaccc     480
tggaacttcc ccgccgccat gatcaccagg aagattggtc ctgccctcgc agccggctgc     540
accgtcgtcg caaagacccc cggtgaaact cccttcacag ccaacgccct cgccgagctg     600
gcccaccgcg ccggcatccc caagggcgtc gtcaacatcg tcaccgcatc ccaaaacacg     660
cccgaggtcg gcgaaaccat caccacccac cccgaggtcc gcaaggtctc cttcaccggc     720
tccaccaacg tcggtaagct cctcatgaag caatcctcgt cgaccatcaa aaaggtgtcc     780
tgggaactag gcgcaacgc cccttcatc gtcttcacg acgtcgagga cctcgacgct     840
gctgtcgccg cgctgtggc ctccaaattc cgtagctctg gacagacctg cgtctgtgca     900
aaccggatct acgtgcagcg cggcatctac gatgaatttg ccaagcgctt cgcagagaag     960
```

-continued

```
gtcaagggct tcaagctggg tgctggcttc gaagaaggcg ttacccacgg tcctgttatt    1020
cacgaccgcg ccgtcaacaa ggtcgacgaa cacgtccgcg acgctgtatc caagggcgcg    1080
caggtcctga cgggtggtca gaaggccgct caccttggtc ctaacttcta cgatttgact    1140
gtcctcacgg agatgaacaa ggatatgctt gtcgcttcag aggagacatt cggccctgtc    1200
gcgggacttt tccccttcga cggaacaa gaagttgtcg acctggctaa caaggctgag     1260
gttggtctgg cgggctactt cttcagcagt aatgttaagc gcatcttccg tgttgcggag    1320
gcgttggagg tcggtatggt gggtgttaac acggggctta ttagtgatgt tgcttcgccg    1380
ttcggtggtg tcaagcagag cggctttggc cgcgagggca gcaagtacgg tattgatgaa    1440
ttcttggtgg tcaagagtgt tactttggga ggaattgagc ctcttcagta g            1491
```

<210> SEQ ID NO 2
<211> LENGTH: 496
<212> TYPE: PRT
<213> ORGANISM: Aspergillus niger

<400> SEQUENCE: 2

```
Met Gly Tyr Thr Val Pro Pro Leu Lys Asp Gln Ser Leu Phe Ile Gln
1               5                   10                  15

Lys Ala Tyr Val Asn Gly Glu Trp Val Asp Ala Gln Ser Gly Gln Thr
            20                  25                  30

Phe Glu Val His Asp Pro Ala Ser Gly Lys Leu Ile Gly Thr Ser Pro
        35                  40                  45

Glu Phe Ser Ala Ala Asp Thr Glu Lys Ala Ile Gln Ala Ala Lys Glu
    50                  55                  60

Ala Phe Pro Lys Phe Arg Thr Thr Leu Ser Arg Glu Arg Ala Arg Met
65                  70                  75                  80

Leu Arg Arg Trp Tyr Gln Leu Met Ile Asp Asn Ala Asp Asp Leu Ala
                85                  90                  95

Thr Leu Ile Thr Trp Glu Asn Gly Lys Pro Leu Thr Ala Lys Gly
            100                 105                 110

Glu Val Asn Tyr Ala Ala Ser Phe Phe Glu Trp Phe Ser Glu Glu Ala
        115                 120                 125

Pro Arg Ile Tyr Gly Asp Thr Ile Pro Ser Ser Val Pro Gly Asn Arg
    130                 135                 140

Val Met Thr Leu Lys Gln Pro Val Gly Val Cys Gly Leu Ile Thr Pro
145                 150                 155                 160

Trp Asn Phe Pro Ala Ala Met Ile Thr Arg Lys Ile Gly Pro Ala Leu
                165                 170                 175

Ala Ala Gly Cys Thr Val Val Ala Lys Thr Pro Gly Glu Thr Pro Phe
            180                 185                 190

Thr Ala Asn Ala Leu Ala Glu Leu Ala His Arg Ala Gly Ile Pro Lys
        195                 200                 205

Gly Val Val Asn Ile Val Thr Ala Ser Gln Asn Thr Pro Glu Val Gly
    210                 215                 220

Glu Thr Ile Thr Thr His Pro Glu Val Arg Lys Val Ser Phe Thr Gly
225                 230                 235                 240

Ser Thr Asn Val Gly Lys Leu Leu Met Lys Gln Ser Ser Ser Thr Ile
                245                 250                 255

Lys Lys Val Ser Trp Glu Leu Gly Gly Asn Ala Pro Phe Ile Val Phe
            260                 265                 270

Asp Asp Val Glu Asp Leu Asp Ala Ala Val Ala Gly Ala Val Ala Ser
```

|  |  | 275 |  |  | 280 |  |  | 285 |  |  |  |
|--|--|--|--|--|--|--|--|--|--|--|--|

Lys Phe Arg Ser Ser Gly Gln Thr Cys Val Cys Ala Asn Arg Ile Tyr
290                     295                     300

Val Gln Arg Gly Ile Tyr Asp Glu Phe Ala Lys Arg Phe Ala Glu Lys
305                         310                         315                 320

Val Lys Gly Phe Lys Leu Gly Ala Gly Phe Glu Glu Gly Val Thr His
                    325                     330                         335

Gly Pro Val Ile His Asp Arg Ala Val Asn Lys Val Asp Glu His Val
                340                     345                     350

Arg Asp Ala Val Ser Lys Gly Ala Gln Val Leu Thr Gly Gly Gln Lys
                    355                     360                     365

Ala Ala His Leu Gly Pro Asn Phe Tyr Asp Leu Thr Val Leu Thr Glu
370                     375                     380

Met Asn Lys Asp Met Leu Val Ala Ser Glu Glu Thr Phe Gly Pro Val
385                     390                     395                     400

Ala Gly Leu Phe Pro Phe Glu Thr Glu Gln Glu Val Val Asp Leu Ala
                    405                     410                     415

Asn Lys Ala Glu Val Gly Leu Ala Gly Tyr Phe Phe Ser Ser Asn Val
                420                     425                     430

Lys Arg Ile Phe Arg Val Ala Glu Ala Leu Glu Val Gly Met Val Gly
                435                     440                     445

Val Asn Thr Gly Leu Ile Ser Asp Val Ala Ser Pro Phe Gly Gly Val
450                     455                     460

Lys Gln Ser Gly Phe Gly Arg Glu Gly Ser Lys Tyr Gly Ile Asp Glu
465                     470                     475                     480

Phe Leu Val Val Lys Ser Val Thr Phe Gly Gly Ile Glu Pro Leu Gln
                    485                     490                     495

<210> SEQ ID NO 3
<211> LENGTH: 1493
<212> TYPE: DNA
<213> ORGANISM: Aspergillus niger

<400> SEQUENCE: 3

```
ctgctctctc tctgctctct ttctgcgctc tctgtgtcgg cactaacccc gaatggggcg      60
ggtatcggca gtccgacgga tctccggggg ccgcacgtcc agcgccgatc gttactcaac     120
cgagcagagg agagagagca gtgagcagtg gtgtcaccga ccataaaaat gcttgcttct     180
gcccatccag ccatcagttg tccagtctgc tccattgtgt gccagtctcg ccccaaggc     240 cgcgcatctg aaaccaaccg gttgggtgaa atcagccggc gggtggcacc cgagcggcca     300
ctggctggga tcatcgcccg caacgcgtca acagcaatca aacgaaggat gcgaaattat     360
tcagcgggcg gttcctttcc aattttccc cgttcctgtc agcatgtcta ctctatcata     420
ctgtaacatt attatattgt gattattttt attctgggtg atgtgtccac tggaccgcac     480
gtggaatgaa gattttcctt ccctcgggac gagaaaccat ggcgcagttg gtgttgtgtg     540
cgtgtgtgtg cgtgtcggtt gtccgaaaat cgccctaaac tccgaggcac gcaccatttg     600
ccattaattc ccttgcgatt gatttctgcc tgtccctgcg accctttgtg acccttgtg      660 acccttgac cctggattca ggggcttggt ggactcatag cgatggggat agggactttt     720
gacccttttg acccttgac cctcccattt tccctggcct aagtacgctg tagtcgtaat     780
tatagaaaga atcttgcgtg gactggggca aagggaac agaacttatc catgtccgag     840
cagcgatcgg ccagtcacca agccggctgg atccgagacc cgctacgtgg gaactcccaa     900
```

| | |
|---|---|
| gagtcgttaa gcaaagccaa gagatcagcc aagatgtcgc tcacgagcct aattgctgga | 960 |
| ttgccatatc gcttgtcgtt gtaccatcgc gtaagatttt atcattgttt ctggggctg | 1020 |
| tcagctagtc taaaacgtac tcctcaaacc agagaggctg atgatgctga tgatgggcct | 1080 |
| ccaccccca aattggtagc gccgttccat gagaggccca gtctctctct gcccgtcctc | 1140 |
| gaccattgtt tggcccagca ctgacacaac cttcaggggg ggccaatgga cgtattccgt | 1200 |
| aggcagcagg caaatgcggc cctaagaact ccccaactaa taagagtcca gactagcaaa | 1260 |
| ggttcgcctc gccggtctcc atctcttcct tcttagtcct cccatttcct ccctcccact | 1320 |
| tggtctctcg ctccagattt cctttcttct ttcatccatc ccatcttgta tccttttgct | 1380 |
| tagcctttt gtttggtttt cttcctctcg ttaaccacca cattcgctct atcttaatac | 1440 |
| aaaccaccca cactcgttct atagcatctg tcttctttcg ttcacctcct cac | 1493 |

<210> SEQ ID NO 4
<211> LENGTH: 2310
<212> TYPE: DNA
<213> ORGANISM: Artificial Sequence
<220> FEATURE:
<223> OTHER INFORMATION: Synthetic DNA

<400> SEQUENCE: 4

| | |
|---|---|
| caattccctt gtatctctac acacaggctc aaatcaataa gaagaacggt tcgtcttttt | 60 |
| cgtttatatc ttgcatcgtc ccaaagctat tggcgggata ttctgtttgc agttggctga | 120 |
| cttgaagtaa tctctgcaga tctttcgaca ctgaaatacg tcgagcctgc tccgcttgga | 180 |
| agcggcgagg agcctcgtcc tgtcacaact accaacatgg agtacgataa gggccagttc | 240 |
| cgccagctca ttaagagcca gttcatgggc gttggcatga tggccgtcat gcatctgtac | 300 |
| ttcaagtaca ccaaccctct tctgatccag tcgatcatcc cgctgaaggg cgctttcgaa | 360 |
| tcgaatctgg ttaagatcca cgtcttcggg aagccagcga ctggtgacct ccagcgtccc | 420 |
| tttaaggctg ccaacagctt tctcagccag gccagccca agaccgacaa ggcctccctc | 480 |
| cagaacgccg agaagaactg gaggggtggt gtcaaggagg agtaagctcc ttattgaagt | 540 |
| cggaggacga agcggtgtca agaggatatt cttcgctctg tattatagat aagatgatga | 600 |
| ggaattggag gtagcatagc ttcatttgga tttgcttttcc aggctgagac tctagcttgg | 660 |
| agcatagagg gtccctttgg cttttcaatat tctcaagtat ctcgagtttg aacttattcc | 720 |
| cgtgaacctt ttattcacca atgagcattg gaatgaacat gaatctgagg actgcaatcg | 780 |
| ccatgaggtt ttcgaaatac atccggatgt cgaaggcttg gggcacctgc gttggttgaa | 840 |
| tttagaacgt ggcactattg atcatccgat agctctgcaa agggcgttgc acaatgcaag | 900 |
| tcaaacgttg ctagcagttc caggtggaat gttatgatga gcattgtatt aaatcaggag | 960 |
| atatagcatg atctctagtt agctcaccac aaaagtcaga cggcgtaacc aaaagtcaca | 1020 |
| caacacaagc tgtaaggatt tcggcacggc tacggaagac ggagaagccc accttcagtg | 1080 |
| gactcgagta ccatttaatt ctatttgtgt ttgatcgaga cctaatacag cccctacaac | 1140 |
| gaccatcaaa gtcgtatagc taccagtgag gaagtggact caaatcgact tcagcaacat | 1200 |
| ctcctggata aactttaagc ctaaactata cagaataaga tggtggagag cttataccga | 1260 |
| gctcccaaat ctgtccagat catggttgac cggtgcctgg atcttcctat agaatcatcc | 1320 |
| ttattcgttg acctagctga ttctggagtg acccagaggg tcatgacttg agcctaaaat | 1380 |
| ccgccgcctc caccatttgt agaaaaatgt gacgaactcg tgagctctgt acagtgaccg | 1440 |
| gtgactcttt ctggcatgcg gagagacgga cggacgcaga gagaagggct gagtaataag | 1500 |

```
cgccactgcg ccagacagct ctggcggctc tgaggtgcag tggatgatta ttaatccggg    1560
accggccgcc cctccgcccc gaagtggaaa ggctggtgtg cccctcgttg accaagaatc    1620
tattgcatca tcggagaata tggagcttca tcgaatcacc ggcagtaagc gaaggagaat    1680
gtgaagccag gggtgtatag ccgtcggcga aatagcatgc cattaaccta ggtacagaag    1740
tccaattgct tccgatctgg taaaagattc acgagatagt accttctccg aagtaggtag    1800
agcgagtacc cggcgcgtaa gctccctaat tgcccatcc  ggcatctgta gggcgtccaa    1860
atatcgtgcc tctcctgctt tgcccggtgt atgaaaccgg aaaggccgct caggagctgg    1920
ccagcggcgc agaccgggaa cacaagctgg cagtcgaccc atccggtgct ctgcactcga    1980
cctgctgagg tccctcagtc cctggtaggc agctttgccc cgtctgtccg cccggtgtgt    2040
cggcggggtt gacaaggtcg ttgcgtcagt ccaacatttg ttgccatatt ttcctgctct    2100
ccccaccagc tgctcttttc ttttctcttt cttttcccat cttcagtata ttcatcttcc    2160
catccaagaa cctttatttc ccctaagtaa gtactttgct acatccatac tccatccttc    2220
ccatccctta ttcctttgaa cctttcagtt cgagctttcc cacttcatcg cagcttgact    2280
aacagctacc ccgcttgagc agacatcacc                                     2310

<210> SEQ ID NO 5
<211> LENGTH: 1020
<212> TYPE: DNA
<213> ORGANISM: Artificial Sequence
<220> FEATURE:
<223> OTHER INFORMATION: Synthetic DNA

<400> SEQUENCE: 5
atgcctgaac tcaccgcgac gtctgtcgag aagtttctga tcgaaaagtt cgacagcgtc      60
tccgacctga tgcagctctc ggagggcgaa gaatctcgtg ctttcagctt cgatgtagga     120
gggcgtggat atgtcctgcg ggtaaatagc tgcgccgatg gtttctacaa agatcgttat     180
gtttatcggc actttgcatc ggccgcgctc ccgattccgg aagtgcttga cattggggaa     240
ttcagcgaga gcctgaccta ttgcatctcc cgccgtgcac agggtgtcac gttgcaagac     300
ctgcctgaaa ccgaactgcc cgctgttctg cagccggtcg cggaggccat ggatgcgatc     360
gctgcggccg atcttagcca gacgagcggg ttcggcccat tcggaccgca aggaatcggt     420
caatacacta catggcgtga tttcatatgc gcgattgctg atccccatgt gtatcactgg     480
caaactgtga tggacgacac cgtcagtgcg tccgtcgcgc aggctctcga tgagctgatg     540
ctttgggccg aggactgccc cgaagtccgg cacctcgtgc acgcggattt cggctccaac     600
aatgtcctga cggacaatgg ccgcataaca gcggtcattg actggagcga ggcgatgttc     660
ggggattccc aatacgaggt cgccaacatc ttcttctgga ggccgtggtt ggcttgtatg     720
gagcagcaga cgcgctactt cgagcggagg catccggagc ttgcaggatc gccgcggctc     780
cgggcgtata tgctccgcat tggtcttgac caactctatc agagcttggt tgacggcaat     840
ttcgatgatg cagcttgggc gcagggtcga tgcgacgcaa tcgtccgatc ggagccggg    900 actgtcgggc gtacacaaat cgcccgcaga agcgcggccg tctggaccga tggctgtgta     960
gaagtactcg ccgatagtgg aaaccgacgc cccagcactc gtccgagggc aaaggaatag   1020

<210> SEQ ID NO 6
<211> LENGTH: 771
<212> TYPE: DNA
<213> ORGANISM: Artificial Sequence
<220> FEATURE:
```

<223> OTHER INFORMATION: Synthetic DNA

<400> SEQUENCE: 6

```
gatccactta acgttactga atcatcaaa cagcttgacg aatctggata taagatcgtt      60
ggtgtcgatg tcagctccgg agttgagaca aatggtgttc aggatctcga taagatacgt    120
tcatttgtcc aagcagcaaa gagtgccttc tagtgattta atagctccat gtcaacaaga    180
ataaaacgcg tttcgggttt acctcttcca gatacagctc atctgcaatg cattaatgca    240
ttggacctcg caaccctagt acgcccttca ggctccggcg aagcagaaga atagcttagc    300
agagtctatt ttcattttcg ggagacgaga tcaagcagat caacggtcgt caagagacct    360
acgagactga ggaatccgct cttggctcca cgcgactata tatttgtctc taattgtact    420
ttgacatgct cctcttcttt actctgatag cttgactatg aaaattccgt caccagcccc    480
tgggttcgca aagataattg cactgtttct tccttgaact ctcaagccta caggacacac    540
attcatcgta ggtataaacc tcgaaaatca ttcctactaa gatgggtata caatagtaac    600
catggttgcc tagtgaatgc tccgtaacac ccaatacgcc ggccgaaact tttttacaac    660
tctcctatga gtcgtttacc cagaatgcac aggtacactt gtttagaggt aatccttctt    720
tctagaagtc ctcgtgtact gtgtaagcgc ccactccaca tctccactcg a             771
```

<210> SEQ ID NO 7
<211> LENGTH: 31
<212> TYPE: DNA
<213> ORGANISM: Artificial Sequence
<220> FEATURE:
<223> OTHER INFORMATION: Synthetic DNA

<400> SEQUENCE: 7

```
ctgcaggatc cacttaaacg ttactgaaat c                                    31
```

<210> SEQ ID NO 8
<211> LENGTH: 28
<212> TYPE: DNA
<213> ORGANISM: Artificial Sequence
<220> FEATURE:
<223> OTHER INFORMATION: Synthetic DNA

<400> SEQUENCE: 8

```
aagcttctcg agtggagatg tggagtgg                                        28
```

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9

```
gaattcctgc tctctctctg ctctctttct                                      30
```

<210> SEQ ID NO 10
<211> LENGTH: 30
<212> TYPE: DNA
<213> ORGANISM: Artificial Sequence
<220> FEATURE:
<223> OTHER INFORMATION: Synthetic DNA

<400> SEQUENCE: 10

```
ggtaccgtga ggaggtgaac gaaagaagac                                      30
```

```
<210> SEQ ID NO 11
<211> LENGTH: 42
<212> TYPE: DNA
<213> ORGANISM: Artificial Sequence
<220> FEATURE:
<223> OTHER INFORMATION: Synthetic DNA

<400> SEQUENCE: 11
gttcacctcc tcacggtacc atgggttaca ctgtccctcc gc                              42

<210> SEQ ID NO 12
<211> LENGTH: 44
<212> TYPE: DNA
<213> ORGANISM: Artificial Sequence
<220> FEATURE:
<223> OTHER INFORMATION: Synthetic DNA

<400> SEQUENCE: 12
taacgtttaa gtggatcgga tccctactga agaggctcaa ttcc                           44

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA

<400> SEQUENCE: 13 caattcccctt gtatctctac acacag                                              26

<210> SEQ ID NO 14
<211> LENGTH: 22
<212> TYPE: DNA
<213> ORGANISM: Artificial Sequence
<220> FEATURE:
<223> OTHER INFORMATION: Synthetic DNA

<400> SEQUENCE: 14
ctcgagtgga gatgtggagt gg                                                   22
```

METHOD FOR INCREASING CITRIC ACID PRODUCTION BY *ASPERGILLUS NIGER* FERMENTATION

TECHNICAL FIELD

The present invention relates to the field of bioengineering technology, and in particular to a method for improving citric acid production by recombinant *Aspergillus niger* strains.

BACKGROUND

Citric acid has broad application prospects and market demand. For economic reasons, some studies have used less expensive raw sugar and agricultural waste to produce citric acid based on existing strains, while others have been devoted to improved strains. Transformation and selection of production strains is the basis of citric acid fermentation industry, determines the success of the fermentation process and the value of the industrialized production of fermentation products. Although citric acid conversion rate is close to the theoretical level in China, the yield can reach 170 g·L$^{-1}$, but the fermentation period last a long time, the industrial production fermentation period is generally 72 h, and the industrial fermentation level needs to be improved. Now, the industry is in a very difficult situation and, according to Alvarez-Vasquez's model, citric acid production by *Aspergillus niger* still has tremendous room to grow, so improvements in citric acid production strains of *Aspergillus niger* have been the focus of attention for decades.

At present, *Aspergillus niger* citric acid industrial production strains are obtained by mutagenesis, a large number of studies are still focused on the industrial production strains using methyl methanesulfonate, nitrosoguanidine, Co-ray, UV, such as single or multiple mutagenesis to breed more productive strains. In recent years, *Aspergillus niger* genome sequencing data has been published, which can construct a comprehensive metabolic network of *Aspergillus niger*. The use of metabolic engineering to transform *Aspergillus niger* can purposefully modify cellular metabolic pathways and reduce the huge workload of mutagenesis breeding screening. Based on the available transcriptome data, it was found that GABA pathway has great influence on citrate synthesis. On the one hand, it supplements the succinic acid needed by TCA cycle and on the other hand improves cell acid resistance. It is expected that GABA pathway may be further enhanced by metabolic transformation.

SUMMARY

In view of the above problems existing in the prior art, the present applicant provides a method for increasing citric acid production by *Aspergillus niger* fermentation. The method of the invention realizes the expression of succinate semialdehyde dehydrogenase SSD in *Aspergillus niger* to enhance the GABA pathway so as to strengthen the TCA cycle and promote the synthesis of citric acid.

The method of the present disclosure is as follows:

Integrates *A. niger* GABA pathway succinate semialdehyde dehydrogenase SSD gene into *A. niger* genome to obtain recombinant *A. niger* strain, the strain is fermented to produce citric acid; the expression of the succinate semialdehyde dehydrogenase SSD gene is regulated by the Pgas promoter.

The nucleotide sequence of the succinate semialdehyde dehydrogenase SSD gene is shown as SEQ ID NO. 1, and the amino acid sequence of the succinate semialdehyde dehydrogenase SSD gene is shown as SEQ ID NO. 2.

The amino acid sequence of the succinate semialdehyde dehydrogenase SSD gene is a sequence obtained by substituting, deleting, or inserting one or more amino acids in the sequence shown in SEQ ID NO.

The Pgas promoter is a low pH-inducible promoter, and the nucleotide sequence of the promoter is shown as SEQ ID NO. 3.

A succinate semialdehyde dehydrogenase SSD gene expression cassette comprising the Pgas promoter, the succinate semialdehyde dehydrogenase SSD gene and the trp terminator, arranged in the order of Pgas-SSD-trp.

The nucleotide sequence of the Pgas promoter is shown in SEQ ID NO. 3; the amino acid sequence of the succinate semialdehyde dehydrogenase SSD gene is shown in SEQ ID NO. 2; the nucleotide of the trp terminator the acid sequence is shown in SEQ ID NO. 6.

The recombinant *A. niger* strain is constructed by:

(1) Construction of succinate semialdehyde dehydrogenase (SSD) gene expression cassette Pgas-SSD-trp;

(2) Construction of expression cassette of resistance gene gpdA-hph-trp;

(3) The gene expression cassette prepared in step (1) and step (2) was transformed into *A. niger*, and the recombinant *A. niger* was obtained through resistance screening and PCR identification.

The gpdA in the expression vector gpdA-hph-trp of the resistance gene is a promoter, and the nucleotide sequence of the promoter is shown as SEQ ID NO. 4.

The nucleotide sequence of the hph gene in the expression vector gpdA-hph-trp of the resistance gene is shown in SEQ ID NO. 5.

The beneficial technical effects of the present invention are as follows:

The present invention utilizes the low pH inducible promoter to initiate the expression of SSD protein in *A. niger* and enhances the production of citric acid by enhancing the GABA pathway. In the method of the invention, the yield of citric acid is improved by 10% with *A. niger* H915-1 as the host; the yield is increased by 45.2% and the time is shortened by 10 hours by fermentation at 42 DEG C.; the yield is increased by 6.4% with the more acidic initial medium.

DETAILED DESCRIPTION

Example 1

(1) Extraction of *Aspergillus niger* RNA: *A. niger* spores were inoculated into citric acid fermentation medium and cultured at 35° C. for 250 r/min for 48 h. The spheroids were collected with mirocloth, washed three times with sterile ultrapure water, Rapidly frozen in liquid nitrogen and thoroughly ground with a liquid nitrogen grinding method. The total RNA was extracted from *A. niger* using the QIAGEN RNeasy Plant Mini Kit, and the cDNA was reverse transcribed into cDNA using TAKARA PrimeScript RT reagent Kit with gDNA Eraser.

(2) Extraction of *A. niger* genomic DNA: *A. niger* spores were inoculated into ME liquid medium (3% malt extract, 0.5% tryptone) and incubated at 35° C. for 250 r/min for 48 h. The spheroids were collected with mirocloth, and the bacteria were washed three times with ultrapure water, drained and quickly frozen in liquid nitrogen. The tissues were thoroughly ground with liquid nitrogen and the filamentous fungus genome was extracted by using DNeasy Plant Mini Kit from QIAGEN.

(3) Construction of SSD protein expression cassette:

① The trp terminator was amplified using pAN7-1 as a template (using the primers trp-F (SEQ ID NO: 7) and trp-R (SEQ ID NO: 8) 6). The sequence contained Pst I and Hin dIII sites upstream and downstream of the sequence, ligated to pMD19, sequenced, digested with the two restriction enzymes, and ligated into the same digested pUC19 to obtain pUC19-trp;

② The Pgas promoter was amplified from the *A. niger* genome using the primers Pgas-F (sequence shown in SEQ ID NO. 9) and Pgas-R (sequence shown in SEQ ID NO. 10) (sequence shown in SEQ ID NO. 3), The two ends of the sequence containing Eco RI and Kpn I restriction sites, digested, the sequence is connected to the same digested pUC19-trp to give pUC-Pgas-trp;

③ RT-PCR amplification of SSD CDS using primers gas-SSD-F (SEQ ID NO: 11) and Trp-SSD-R (SEQ ID NO: 12). The sequences contained pUC-Pgas-trp about 20 bp homologous sequences at both ends respectively. Homologous recombination was performed using the Vazyme One Step Clone Kit to form a gas-SSD-trp expression cassette to obtain pGSH expression vector;

The primers used are as follows:

```
trp-F:
ctgcagGATCCACTTAAACGTTACTGAAATC trp-R:
aagcttCTCGAGTGGAGATGTGGAGTGG

Pgas-F:
gaattcCTGCTCTCTCTCTGCTCTCTTTCT

Pgas-R:
ggtaccGTGAGGAGGTGAACGAAAGAAGAC

Gas-SSD-F:
gttcacctcctcacGGTACCATGGGTTACACTGTCCCTCCGC

Trp-SSD-R:
TAACGTTTAAGTGGATCGGATCCCTACTGAAGAGGCTCAATTCC
```

(4) Preparation and transformation of *A. niger* protoplasts:

① Inoculate *A. niger* spores into PDA liquid medium at a concentration of $3 \times 10^5$/ml and incubate at 200 r/min overnight at 30° C. Collect the fungus spheres with mirocloth and wash the spheroids with sterile water.

② Weigh 0.5 g/L lysing enzyme, and dissolved with osmotic pressure stabilizer KMC, sterilized by sterile filter, weighed 0.5 g mycosphere, added to the enzyme solution, 37° C., 100 r/min shaking culture About 3 h until the hypha completely digested as protoplasts, centrifuged at 1000 rpm for 10 min at 4° C., the supernatant was discarded, the same volume of precooled STC was added, and centrifuged at 1000 rpm for 10 min at 4° C. The supernatant was washed twice, and add 100 µL STC, mix well to obtain *A. niger* protoplasm;

③ Add 10 µL linearized nucleic acid fragment and 330 µL PEG buffer to 100 µL protoplast of *A. niger*, place on ice for 20 min, add 2 mL PEG, place at room temperature for 10 min, add 4 mL STC and 4 mL at 48° C. Preheated supernatant was plated on the bottom medium containing 180 mg/L hygromycin. Plates are incubated at 35° C. for up to 4-7 days until colonies appear, picking single colonies for generations. Three single spore subcultures per colony.

Control Example 1

(1) Acquisition of hygromycin resistance expression cassette: The hygromycin-resistant expression cassette was obtained from the plasmid pAN7-GFP by primers gpd-F (sequences shown in SEQ ID NO. 13) and Ttrp-R-2, the expression cassette comprises PgpdA (SEQ ID NO: 4), hph (SEQ ID NO: 5) and trp terminator (SEQ ID NO: 6).

```
gpd-F:
CAATTCCCTTGTATCTCTACACACAG

Ttrp-R-2:
CTCGAGTGGAGATGTGGAGTGG
```

(2) Preparation and transformation of *Aspergillus niger* protoplasts:

① inoculate *A. niger* spores into PDA liquid medium at a concentration of $3 \times 10^5$/ml, incubate at 200 r/min overnight at 30° C., collect spheroids with mirocloth, and sterilize the spheroids with sterile water;

② Weigh 0.5 g/L lysing enzyme, and dissolved with osmotic pressure stabilizer KMC, sterilized by sterile filter, weighed 0.5 g mycosphere, added to the enzyme solution, 37° C., 100 r/min shaking culture 3 h until the hypha completely digested as protoplasts, centrifuged at 1000 rpm for 10 min at 4° C., the supernatant was discarded, the same volume of precooled STC was added, centrifuged at 1000 rpm for 10 min at 4° C., the supernatant was discarded, washed twice and added with 100 µL STC, mixing, preparation of *A. niger* protoplasts;

③ Add 10 µL linearized nucleic acid fragment and 330 µL PEG buffer to 100 µL protoplast of *A. niger*, place on ice for 20 min, add 2 mL PEG, place at room temperature for 10 min, add 4 mL STC and 4 mL at 48° C. The pre-warmed upper culture medium was plated on an underlayer medium containing 180 mg/L hygromycin and the plates were inverted at 35° C. for 4-7 days until colonies appeared, single colonies were picked and subcultured, and each colony was subjected to 3 Sub-single spores sub-generation.

Tests

The *A. niger* obtained in the examples and the control examples, the commonly used *A. niger* Co82 and the *Aspergillus niger*TN-A09 were respectively inoculated on PDA medium (malt extract 30 g/L, tryptone 5 g/L) Spores were scraped at 35° C. for 7 days, spores were harvested and seeded in seed culture medium (cornstarch medium, total sugar content 10%, total nitrogen content 0.2%) at $10^6$/mL inoculum, 37° C., 250 r/min culture 24 h. The fermentation medium was transferred to 1/10 inoculum and fermented at 35° C. and 250 r/min for 72 h. The fermentation broth was centrifuged to remove the bacteria and diluted 10-fold. The content of citric acid was determined by HPLC after filtration through the membrane. The test data is shown in Table 1.

TABLE 1

|  | Citric acid content (g/100 mL) | Conversion rate (%) | Fermentation cycle (h) |
|---|---|---|---|
| Implementation example | 17.6 | 98 | 55 |
| Cotrol example | 13.4 | 92 | 60 |
| *A. niger* Co82 | 13 | 92 | 60 |
| *A. niger* TN-A09 | 12.5 | 92 | 60 |

Note:
citric acid content detection using Agilent 1200 HPLC (with UV-visible detector, differential detector and workstation); chromatographic conditions: HPX87 H column (4.6 × 250 mm, 5 µm), the mobile phase of 5 mM sulfuric acid solution, The flow rate of 0.6 mL/min, the injection volume of 10 µL, the column temperature of 30° C., 210 nm wavelength UV detection.

It can be seen from Table 1 that the strains prepared in the examples of the present invention have short fermentation time and better citric acid yield and conversion rate than the control and the existing *A. niger* strains.

(2) The *A. niger* obtained in the examples and the comparative examples was inoculated into the 35° C. spore culture 7 on the ME medium (malt extract 30 g/L, tryptone 5 g/L) with the commonly used *A. niger* zjs-8 The spores were scraped and inoculated into seed medium (cornstarch medium, total sugar content 10%, total nitrogen content 0.2%) at $10^6$/mL inoculum, cultured at 37° C. and 250 r/min for 24 h, 10 inoculum transfer fermentation medium, 42° C., 250 r/min fermentation 72 h. The fermentation broth was centrifuged to remove the bacteria, diluted 10 times, and the citric acid content was detected by HPLC after being filtered through a membrane filter. The test results are shown in Table 2.

TABLE 2

|  | Citric acid content (g/100 mL) | Conversion rate (%) | Fermentation cycle (h) |
|---|---|---|---|
| Implementation example | 16.5 | 97 | 60 |
| Control example | 10.7 | 66.8 | 70 |
| *A. niger* zjs-8 | 10 | 61.83 | 60 |

As can be seen from the data in Table 2, the *A. niger* strains prepared in the examples of the present invention have good high temperature resistance, and citric acid yield and conversion rate are still higher than those of the existing *A. niger* zjs-8 under the condition of increasing temperature.

(3) *A. niger* and *A. niger* Co82 obtained in the examples and the control examples were respectively inoculated on ME medium (malt extract 30 g/L, tryptone 5 g/L) for 35 days at 35° C. for 7 days to sporulate the spores, The inoculation amount of $10^6$/mL was inoculated into the seed medium (corn starch medium, the total sugar content of 10%, the total nitrogen content of 0.2%, pH 3.5), 37° C., 250 r/min culture 24 h, Transfer fermentation medium (pH 2.0), 42° C., 250 r/min fermentation 72 h. The fermentation broth was centrifuged to remove the bacteria, diluted 10 times, and the citric acid content was detected by HPLC after being filtered through a membrane filter. The test results are shown in Table 3.

TABLE 3

|  | Citric acid content (g/100 mL) | Conversion rate (%) | Fermentation cycle (h) |
|---|---|---|---|
| Implementation example | 18.3 | 99 | 60 |
| Comparative example | 14 | 93 | 60 |
| *Aspergillus niger* Co82 | 13 | 93 | 65 |

It can be seen from Table 3 that the strains obtained in the examples of the present invention still have better citric acid yield and conversion under more severe acidic conditions and relatively short fermentation cycles. The recombinant strains of the present invention have better Acid resistance.

What is claimed is:

1. A recombinant *Aspergillus niger* strain, comprising:
a genome comprising an inserted *Aspergillus niger* gamma-aminobutyric acid (GABA) pathway succinate semialdehyde dehydrogenase (SSD) gene, wherein the GABA pathway SSD gene is under control of a Pgas promoter,
wherein the GABA pathway SSD gene is set forth in SEQ ID NO:1,
wherein the Pgas promoter sequence is SEQ ID NO:3,
wherein the *A. niger* strain produces a higher amount of citrate as compared with a wild type *A. niger* strain grown under identical conditions.

2. The recombinant *A. niger* strain of claim 1, wherein the SSD gene produces a protein having an amino acid sequence set forth in SEQ ID NO: 2.

3. The recombinant *A. niger* strain of claim 1, wherein the Pgas promoter is induced by a low pH of between pH 2.0 and pH 3.5.

4. The recombinant *Aspergillus niger* strain of claim 1, wherein the gene sequence of GABA pathway SSD gene and the Pgas promoter are encoded onto an expression cassette transformed into the *A. niger* strain.

5. The recombinant *Aspergillus niger* strain of claim 4, wherein the expression cassette further comprises at least one trp terminator sequence of SEQ ID NO:6.

6. The recombinant *Aspergillus niger* strain of claim 4, wherein the expression cassette further comprises a gpdA promoter sequence of SEQ ID NO:4.

7. The recombinant *Aspergillus niger* strain of claim 4, wherein the expression cassette further comprises a hygromycin resistance (hph) gene sequence of SEQ ID NO:5.

8. The recombinant *Aspergillus niger* strain of claim 4, wherein the expression cassette encodes a trp terminator sequence of SEQ ID NO:6, a gpdA promoter sequence of SEQ ID NO:4, and an hgh gene sequence of SEQ ID NO:5.

9. The recombinant *Aspergillus niger* strain of claim 8, wherein the expression cassette sequences are in the order of gpdA-hph-trp and Pgas-SSD-trp.

10. The recombinant *Aspergillus niger* strain of claim 1, wherein the *A. niger* strain is derived from *A. niger* strain H915-1.

11. The recombinant *Aspergillus niger* strain of claim 1, wherein the amount of citrate produced by the *A. niger* strain is at least 10% higher under identical conditions than a corresponding wild type *Aspergillus niger* strain.

12. The recombinant *Aspergillus niger* strain of claim 1, wherein the amount of citrate produced by the *A. niger* strain is at least 45.2% higher under identical conditions than a corresponding wild type *Aspergillus niger* strain.

13. An expression cassette of succinate semialdehyde dehydrogenase SSD, comprising a promoter Pgas, a succinate semialdehyde dehydrogenase SSD gene and a terminator trp in order of Pgas-LGT1-trp.

14. The expression cassette in claim 13, wherein a sequence of the promoter Pgas is set forth in SEQ ID NO: 3, an amino acid sequence of succinate semialdehyde dehydrogenase SSD is set forth in SEQ ID NO: 2, and a sequence of terminator trp is set forth in SEQ ID NO: 6.

15. A method for the reconstruction of reconstructed *A. niger* mentioned in claim 1 contains the following steps:
    (1) constructing an expression cassette of succinate semialdehyde dehydrogenase with Pgas-SSD-trp;
    (2) constructing a resistant gene expression cassette gpdA-hph-trp;
    (3) inserting expression cassettes in step (1) and (2) into *A. niger*, screening resistant strains and confirming reconstructed strains with PCR.

16. The method in claim 15, wherein a sequence of gpdA promoter in resistant gene cassette is set forth in SEQ ID NO: 4.

17. The method in claim 15, wherein a sequence of resistant gene hph in resistant gene cassette is set forth in SEQ ID NO: 5.

18. A method of expressing citric acid from *Aspergillus niger*, which comprises:
    incubating an *A. niger* strain in growth medium comprising malt extract and tryptone at 35° C. for seven days to generate spores, wherein the *A. niger* strain comprises a genome comprising a gamma-aminobutyric acid (GABA) pathway succinate semialdehyde dehydrogenase (SSD) gene, wherein the SSD gene is under the control of a Pgas promoter, wherein the SSD gene sequence is SEQ ID NO:1, and wherein the Pgas promoter sequence is SEQ ID NO:3,
    harvesting the spores,
    inoculating seed culture medium with the harvested spores at a density of $10^6$ spores per mL to generate a seed culture, wherein the seed medium comprises corn starch medium comprising a total sugar concentration of 10% and a total nitrogen concentration of 0.2%,
    growing the spores in the seed culture medium at 37° C. for 24 hours at pH 3.5,
    inoculating a fermentation medium with the seed culture at 1/10 volume,
    incubating the fermentation medium for 72 hours at 35° C. at pH 2.0, and
    centrifuging the fermentation medium and discarding bacteria to obtain citric acid.

19. The method of claim 18, wherein the *A. niger* strain produces a higher amount of citrate as compared with a wild type *A. niger* strain grown under identical conditions.

20. The method of claim 18, wherein the *A. niger* strain produces between 10% and 45.2% more citrate as compared with a wild type *A. niger* strain under identical conditions.

* * * * *